(12) United States Patent
Rogatchev et al.

(10) Patent No.: US 7,029,457 B2
(45) Date of Patent: Apr. 18, 2006

(54) JET INJECTOR WITH HAND PIECE

(75) Inventors: Victor T. Rogatchev, Voronezh (RU); Patrick B. McCalmon, Weatherby Lake, MO (US)

(73) Assignee: Felton International, Inc., Lenexa, KS (US)

( * ) Notice: Subject to any disclaimer, the term of this patent is extended or adjusted under 35 U.S.C. 154(b) by 70 days.

(21) Appl. No.: 10/269,570

(22) Filed: Oct. 11, 2002

(65) Prior Publication Data

US 2003/0088207 A1 May 8, 2003

Related U.S. Application Data

(63) Continuation-in-part of application No. 09/717,548, filed on Nov. 21, 2000, now Pat. No. 6,770,054.

(60) Provisional application No. 60/386,457, filed on Jun. 4, 2002, provisional application No. 60/361,198, filed on Mar. 1, 2002, provisional application No. 60/329,082, filed on Oct. 12, 2001.

(51) Int. Cl.
*A61M 37/00* (2006.01)
(52) U.S. Cl. ........................ 604/140; 604/131
(58) Field of Classification Search ................ 604/187, 604/140, 70, 198, 72, 131, 68, 207, 69
See application file for complete search history.

(56) References Cited

U.S. PATENT DOCUMENTS

| | | | |
|---|---|---|---|
| 204,639 A | 6/1878 | Willis et al. | |
| 235,348 A | 12/1880 | Hjertman | |
| 1,837,932 A * | 12/1931 | Weigle | 128/200.19 |
| 2,653,602 A * | 9/1953 | Smoot | 604/68 |
| 2,821,981 A | 2/1958 | Ziherl et al. | |
| 3,057,349 A | 10/1962 | Ismach | |
| 3,202,151 A | 8/1965 | Kath | |
| 3,292,622 A | 12/1966 | Banker | |
| 3,490,451 A | 1/1970 | Yahner | |
| 3,515,130 A * | 6/1970 | Tsujino | 604/70 |
| 3,518,990 A | 7/1970 | Banker | |
| 3,526,225 A | 9/1970 | Isobe | |
| 3,561,443 A | 2/1971 | Banker | |
| 3,714,943 A * | 2/1973 | Yanof et al. | 604/70 |
| 3,859,996 A * | 1/1975 | Mizzy et al. | 604/70 |

(Continued)

FOREIGN PATENT DOCUMENTS

EP 0347190 A1 12/1989

(Continued)

OTHER PUBLICATIONS

*Cool.Click: A Needle-Free Device For Growth Hormone Delivery*, The Medical Letter, vol. 43, No. 1095, pp. 2-3 (Jan. 8, 2001).

(Continued)

*Primary Examiner*—Manuel Mendez
(74) *Attorney, Agent, or Firm*—Joseph A. Mahoney; Mayer Brown Rowe & Maw LLP

(57) ABSTRACT

The present invention relates to a jet injector system with a hand piece. The present invention generally comprises a power unit, a medicine unit, an energy unit, a supply bottle, and a hand piece. The hand piece and power unit may be separate components connected to each other by a high pressure hose, which gives the user more flexibility. A valve assembly having a ball lock assembly and a needle assembly controls the release of medication from the high pressure hose into the hand piece and out a nozzle into the subject.

12 Claims, 10 Drawing Sheets

U.S. PATENT DOCUMENTS

| | | | |
|---|---|---|---|
| 3,933,155 | A | 1/1976 | Johnston |
| 4,007,739 | A | 2/1977 | Bron et al. |
| 4,059,107 | A | 11/1977 | Iriguchi et al. |
| D248,568 | S | 7/1978 | Ismach |
| 4,103,684 | A | 8/1978 | Ismach |
| 4,266,541 | A | 5/1981 | Landau |
| 4,400,171 | A | 8/1983 | Dettbarn et al. |
| 4,403,986 | A | 9/1983 | Dettbarn et al. |
| 4,592,742 | A | 6/1986 | Landau |
| 4,596,556 | A | 6/1986 | Morrow et al. |
| 4,642,095 | A | 2/1987 | Dettbarn et al. |
| 4,850,967 | A | 7/1989 | Cosmai |
| 4,913,699 | A | 4/1990 | Parsons |
| 5,009,637 | A | 4/1991 | Newman et al. |
| 5,024,656 | A | 6/1991 | Gasaway et al. |
| 5,049,125 | A | 9/1991 | Accaries et al. |
| 5,063,905 | A | 11/1991 | Farrell |
| 5,064,413 | A * | 11/1991 | McKinnon et al. ............ 604/70 |
| 5,176,645 | A * | 1/1993 | Guerrero ..................... 604/143 |
| 5,256,142 | A | 10/1993 | Colavecchio |
| 5,312,335 | A | 5/1994 | McKinnon et al. |
| 5,383,851 | A | 1/1995 | McKinnon et al. |
| 5,399,163 | A | 3/1995 | Peterson et al. |
| 5,501,666 | A | 3/1996 | Spielberg |
| 5,503,627 | A | 4/1996 | McKinnon et al. |
| 5,520,639 | A | 5/1996 | Peterson et al. |
| 5,569,190 | A | 10/1996 | D'Antonio |
| 5,599,302 | A | 2/1997 | Lilley et al. |
| 5,599,309 | A | 2/1997 | Marshall et al. |
| 5,618,268 | A | 4/1997 | Raines et al. |
| 5,643,211 | A | 7/1997 | Sadowski et al. |
| 5,697,917 | A | 12/1997 | Sadowski et al. |
| 5,722,953 | A | 3/1998 | Schiff et al. |
| 5,746,714 | A | 5/1998 | Salo et al. |
| 5,800,388 | A | 9/1998 | Schiff et al. |
| 5,840,061 | A | 11/1998 | Menne et al. |
| 5,840,062 | A | 11/1998 | Gumaste et al. |
| 5,846,233 | A | 12/1998 | Lilley et al. |
| 5,865,795 | A | 2/1999 | Schiff et al. |
| 5,865,796 | A | 2/1999 | McCabe |
| 6,053,889 | A | 4/2000 | Heinzen et al. |
| 6,080,130 | A | 6/2000 | Castellano |
| 6,083,197 | A | 7/2000 | Umbaugh |
| 6,096,002 | A | 8/2000 | Landau |
| 6,102,896 | A | 8/2000 | Roser |
| 6,135,979 | A | 10/2000 | Weston |
| 6,241,709 | B1 | 6/2001 | Bechtold et al. |
| 6,258,062 | B1 | 7/2001 | Thielen et al. |

FOREIGN PATENT DOCUMENTS

| | | |
|---|---|---|
| EP | 0526772 A1 | 2/1993 |
| EP | 0776224 B1 | 12/1998 |
| EP | 0788386 B1 | 1/1999 |
| EP | 0888790 A1 | 1/1999 |
| EP | 0888791 A1 | 1/1999 |
| EP | 0799064 B1 | 8/1999 |
| EP | 0951917 A2 | 10/1999 |
| FR | 2629348 | 10/1989 |
| FR | 2641190 | 7/1990 |
| RO | 0106078 | 2/1993 |
| RO | 0108150 | 2/1994 |
| RU | 2008932 | 3/1994 |
| RU | 2108117 | 4/1998 |
| SU | 0257697 | 11/1969 |
| SU | 0373005 | 3/1973 |
| SU | 0573160 | 11/1977 |
| SU | 0835448 | 7/1979 |
| SU | 0793580 | 1/1981 |
| SU | 0835449 | 6/1981 |
| SU | 0957914 | 9/1982 |
| SU | 1107874 | 8/1984 |
| SU | 1144705 | 3/1985 |
| SU | 1168261 | 7/1985 |
| SU | 1219093 | 3/1986 |
| SU | 1230600 | 5/1986 |
| SU | 1271524 | 11/1986 |
| SU | 1279636 | 12/1986 |
| SU | 1560201 | 4/1990 |
| SU | 1839093 | 12/1993 |
| WO | 9734652 A1 | 9/1997 |
| WO | 9813470 A1 | 4/1998 |
| WO | 9820921 A1 | 5/1998 |
| WO | 9901168 A1 | 1/1999 |
| WO | 9901169 A1 | 1/1999 |
| WO | 9903529 A2 | 1/1999 |

OTHER PUBLICATIONS

Figge, et al., *Anatomic Evaluation of a Jet Injection Instrument Designed to Minimize Pain and Inconvenience of Parental Therapy*, The American Practitioner, vol. 3, No. 4, pp. 197-206 (Dec. 1948).

Brochure on Agro-Jet: Needle-Less Jet Injector by M.I.T.

Description and Operating Instructions for Hydraulic Needleless Injector by .V/O Medexport in Moscow.

Dimache, et al., *A Clinical, Epidemiological and Laboratory Study on Avoiding the Risk of Transmitting Viral Hepatitis During Vaccinations with the Dermojet Protected by an Anticontaminant Disposable Device*, Vaccine, vol. 15, No. 8, pp. 1010-1013 (1997).

Jet Gun Injection Transmission: *A Clinical, Epidemiological and Laboratory Study on Avoiding the Risk of Transmitting Viral Hepatitis During Vaccinations with the Dermojet Protected by an Anticontaminant Disposable Device*, American Journal of Injection Control, vol. 26, No. 4, pp. 442-445 (Aug. 1998).

\* cited by examiner

JET INJECTOR WITH HAND PIECE

CROSS REFERENCE TO RELATED APPLICATIONS

Pursuant to 35 U.S.C. §§ 119(e) and 120, this application (1) is a continuation-in-part of U.S. application Ser. No. 09/717,548, filed Nov. 21, 2000, now U.S. Pat. No. 6,770,054 which claims priority to prior Russian Application No. 99124267, filed Nov. 23, 1999; (2) claims priority to prior U.S. provisional application No. 60/329,082, filed Oct. 12, 2001; (3) claims priority to prior U.S. provisional application No. 60/361,198, filed Mar. 1, 2002; and (4) claims priority to prior U.S. provisional application No. 60/386,457, filed Jun. 4, 2002, the disclosures of which are incorporated herein by reference.

FIELD OF THE INVENTION

The present invention relates to needle-free injector systems, and more particularly to high work-load needle-free drug delivery devices for animal and human health applications.

BACKGROUND OF THE INVENTION

For many years, vaccination and administration of medicine has been accomplished by using syringes and needles. However, use of syringes and needles increases the risk of disease transmission among injection recipients. In addition, syringes and needles may cause tissue damage at the site of injection, thereby creating lesions and scar tissue. Particularly with the use of needle injection of animals, injection site lesions may result in losses of tens of millions of dollars each year to meat producers from reduced grade and carcass trim. Further, during injection needle tips may break causing residual needle fragments to remain in the subject. With animal use, this may further result in needle fragments entering into the food system. Disposable needles and syringes also create hazardous medical waste and waste disposal problems. A further drawback to disposable syringes and needles are the high costs when the units are provided for worldwide use. Many subjects, whether human or animal, have a strong aversion to needle injection. Accordingly, there exists a need for alternative methods of delivering medication to patients.

Alternative methods of delivering medication have been developed. One known method is to deliver medication using a needle-free injector. A needle-free injector delivers medication by providing a strong, high pressure blast of the medication through a small orifice, which causes a minute stream of the medication to exit the orifice at a high rate of speed, thereby allowing the medication to penetrate into the skin and subcutaneous tissues. A substantial amount of pressure is needed to create a high rate of speed of the medication. As a result, needle-free injectors are typically bulky and cumbersome to use. Further, accidental firing of the injector may cause misdosing of subjects and loss of medicine.

There is a need in the world health industry for a safe, economical, high work-load injection system to prevent and eradicate certain diseases in animals and humans.

SUMMARY OF THE INVENTION

The present invention is directed to a jet injector system with a separate hand piece. It generally comprises a power unit, a medicine unit, an energy unit, a supply bottle, and a hand piece. The hand piece and power unit may be separate components connected to each other by a high pressure hose, which gives the user more flexibility. A valve assembly having a ball lock assembly and a needle assembly controls the release of medication from the high pressure hose into the hand piece and out a nozzle into the subject. Separating the components allows for a smaller hand piece that is easier to control and handle.

DETAILED DESCRIPTION

Figure 1:
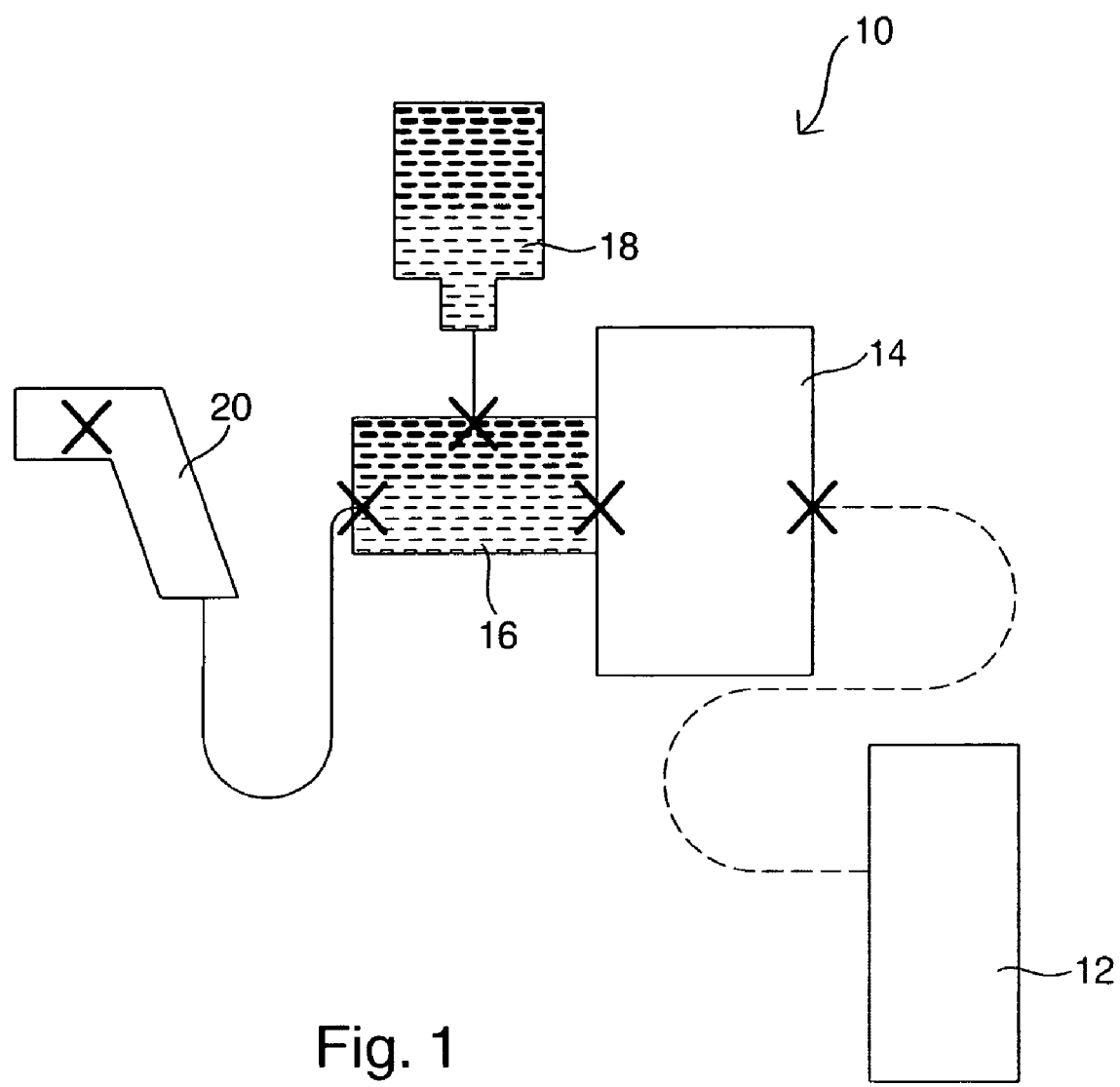
FIG. 1 is a block diagram of major components of the injection system of the present invention.

FIG. 1 depicts an injector 10 for injecting a human or an animal with a vaccine or other type of medication. The injector 10 has an energy unit 12, a power unit 14, a medicine unit 16, a supply bottle 18, and a hand piece 20. Critical interfaces, where each of these components connect, are illustrated as "X." A more detailed description of these interfaces is described below in reference to FIGS. 2 and 3.

Figure 2:
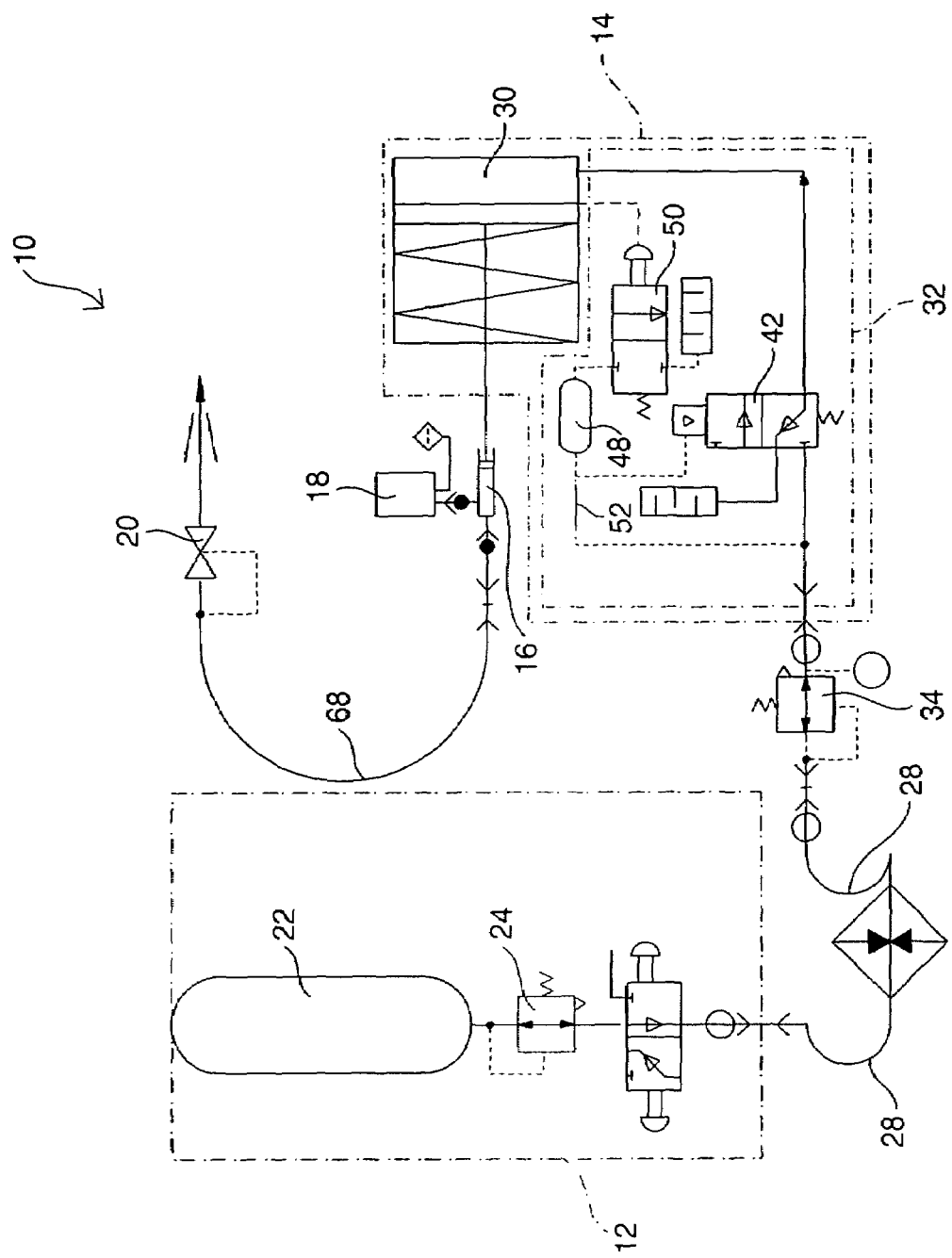
FIG. 2 is a schematic view of one embodiment of the injection system of the present invention.
Figure 3:
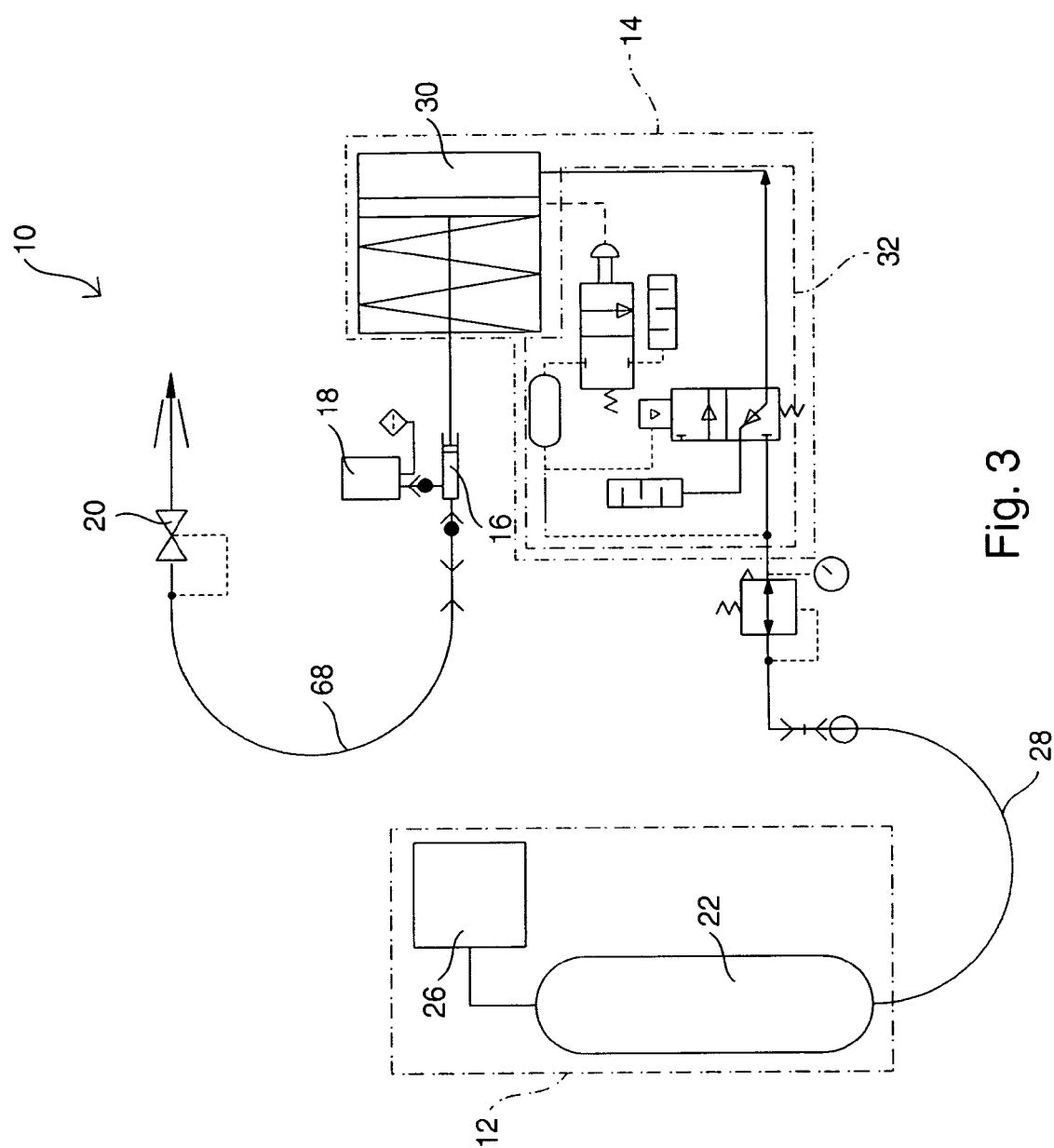
FIG. 3 is a schematic view of another embodiment of the injection system of the present invention.

FIG. 2 depicts a schematic of the injector 10. The energy unit 12 may include a gas cylinder 22 connected to a regulator 24. In one embodiment, the gas cylinder 22 is a reusable carbon dioxide canister. In one embodiment, the regulator 24 regulates gas pressure from 50 to 120 psi. The energy unit 12 provides compressed regulated air or other gas to the power unit 14. This may be accomplished by a compressor 26 (FIG. 3) or by a pre-filled cylinder. The compressor 26 may be portable or stationary. If a portable compressor 26 is used then batteries or an AC power connection will supply electrical power (not shown). Gas cylinders 22 of various sizes may be utilized to hold varying amounts of gas. In one embodiment, the gas cylinder 22 holds liquid carbon dioxide.

The energy unit 12 supplies energy to the power unit 14. A hose 28 may be used to connect the energy unit 12 to the power unit 14. In one embodiment the hose length between the energy unit 12 and power unit 14 is approximately 300 mm.

Figure 4:
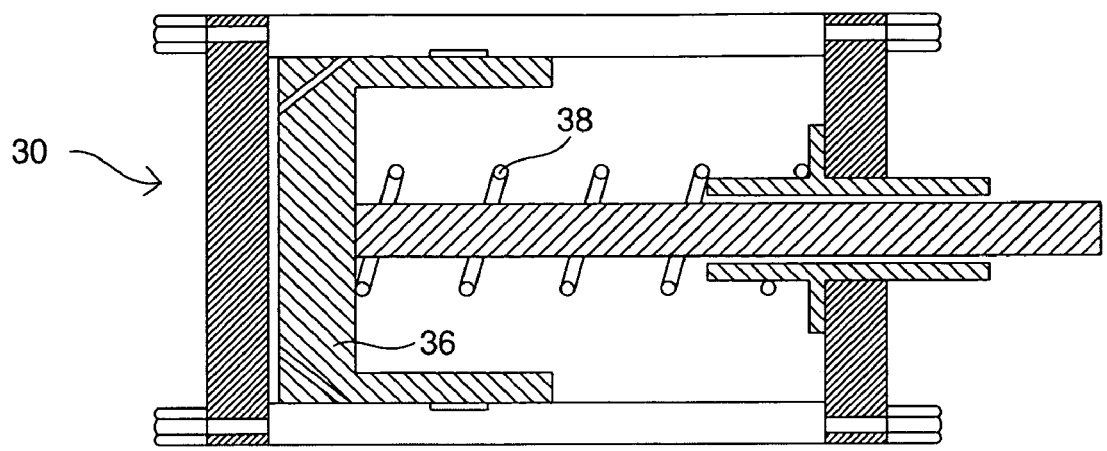
FIG. 4 is a cross section of one embodiment of the amplifier of the present invention.
Figure 5:
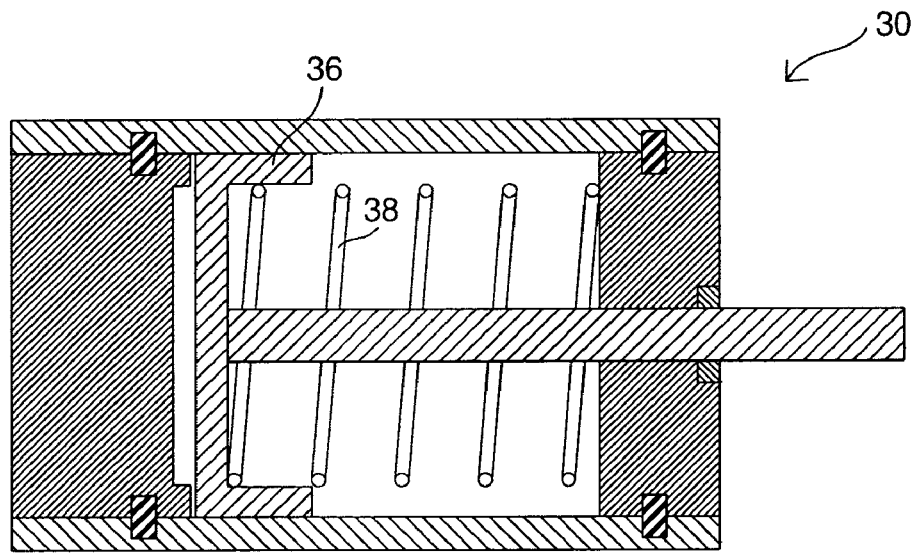
FIG. 5 is a cross section of another embodiment of the amplifier of the present invention.

The power unit 14 comprises an amplifier 30 and an air distribution system 32. The amplifier 30 converts pneumatic energy to hydraulic pressure to pressurize the medicine unit 16 for both filling the medicine from the supply bottle 18 to the medicine unit 16 and dispensing the medicine from the medicine unit 16 to the hand piece 20. As depicted in FIG. 4, the amplifier 30 may include a power piston 36 connected to a refill spring 38. The pressure created by the amplifier 30 may be varied to accommodate varying subject sizes by using a regulator 34 (FIG. 2). Higher operational pressures will deposit the medication more deeply and quickly. Lower pressures will inject the dose less deeply. The amplifier 30 of FIG. 4 may be used as a build able amplifier. FIG. 5 depicts an alternate embodiment of the amplifier 30 of the present invention. The amplifier of FIG. 5 may be a disposable amplifier 30 designed for a predetermined service life.

Figure 6:
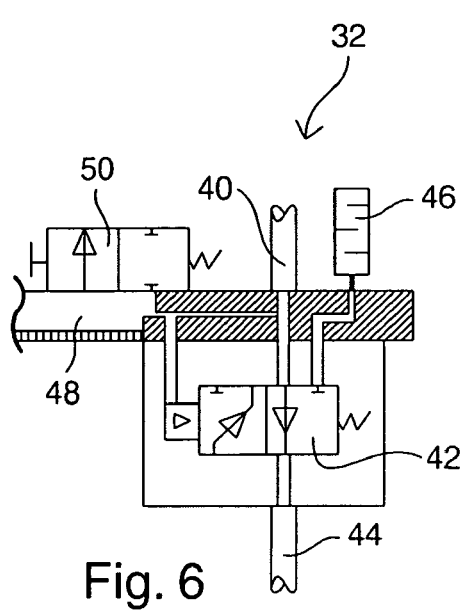
FIG. 6 is a schematic view of the air distributor of the present invention.

The air distribution system 32 supplies and controls the air flow into and out of the amplifier 30. As depicted in FIG. 6, gas travels through a supply line 40 from the regulator 34 (FIG. 2) into the air distribution system 32, first entering a three way piloted valve 42, which has two positions or a vent valve 50. In position one, the piloted valve 42 exhausts the air from the amplifier 30 to the atmosphere via a muffler 46. In position two, the piloted valve 42 releases air to an exit line 44 to the amplifier 30. When the system is not pressurized, compressed air travels from the supply line 40 into a pilot chamber 48 through a narrow passage 52 that controls the refill rate. The gas in the pilot chamber 48 is controlled by the vent valve 50. The vent valve 50 is mechanically actuated by the movement of the power piston 36 in the amplifier 30.

When the injector 10 is pressurized, vent valve 50 is closed and air from regulator 34 travels to piloted valve 42. The piloted valve 42 is in the second position when the injector 10 is pressurized and directs the air to the back side of power piston 36 in amplifier 30. When power piston 36 reaches the end of its stroke after an injection, no pressure remains in piloted valve 42, thereby causing piloted valve 42 to change to the first position allowing air from amplifier 30 to exhausts out of muffler 46. The vent valve 50 then closes and the three way piloted valve 42 opens back to the second position, causing air to travel to the amplifier 30.

The amplifier 30 then connects to the medicine unit 16 and may be integral with the medicine unit 16 as depicted in FIG. 1. The medicine unit 16 includes a piston rod 76 that controls the movement of medication within the medicine unit 16. The medicine unit 16 is attached to or connected to the supply bottle 18. The supply bottle 18 may be a conventional bulk medicine bottle 18 that is connected to the medicine unit 16 via an inlet tube 80 and a standard vent spike assembly (not shown). Alternatively, flexible medicine pouches (not shown) can be utilized in which only an un-vented spike assembly would be required. It is possible that the vent spike assembly be modified to provide proprietary connections for specific medications and to ensure that medications are not used with the wrong injector 10.

Figure 7:
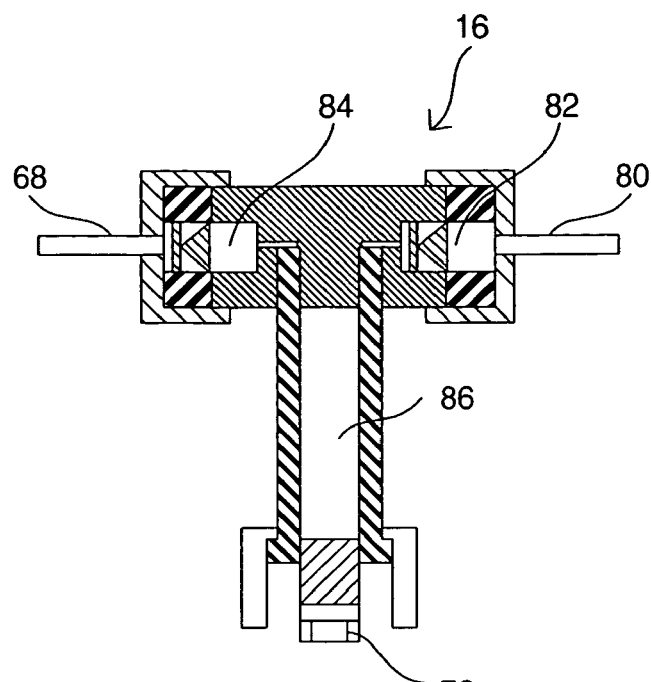
FIG. 7 is a cross section of one embodiment of the medicine chamber of the present invention.

As depicted in FIG. 7, the medicine unit 16 includes an inlet valve 82 to receive the medicine from the inlet tube 80 and an outlet valve 84 to control the flow of the medicine out of the medicine unit 16 and into a high pressure hose 68 to the hand piece 20. A high pressure chamber 86 enclosed on one end by the piston rod 76 is located between the inlet valve 82 and the outlet valve 84 to store the medication after filling the medicine unit 16 and prior to injection. The size of the high pressure chamber 86 may be adjusted to accommodate various doses. In one embodiment, the diameter of high pressure chamber 86 is 8 mm and the diameter of the high pressure hose 68 is 2 mm. In one embodiment, the high pressure chamber 86 is sized to propel a 2 ml dose of medication to the subject.

Figure 8:
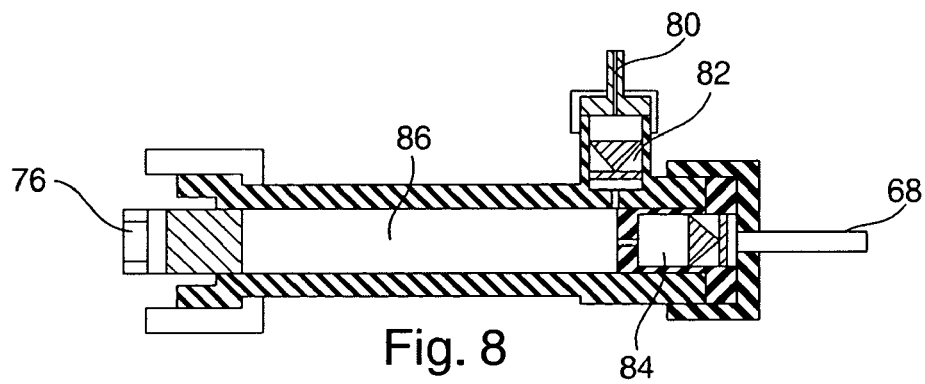
FIG. 8 is a cross section of another embodiment of the medicine chamber of the present invention.
Figure 9:
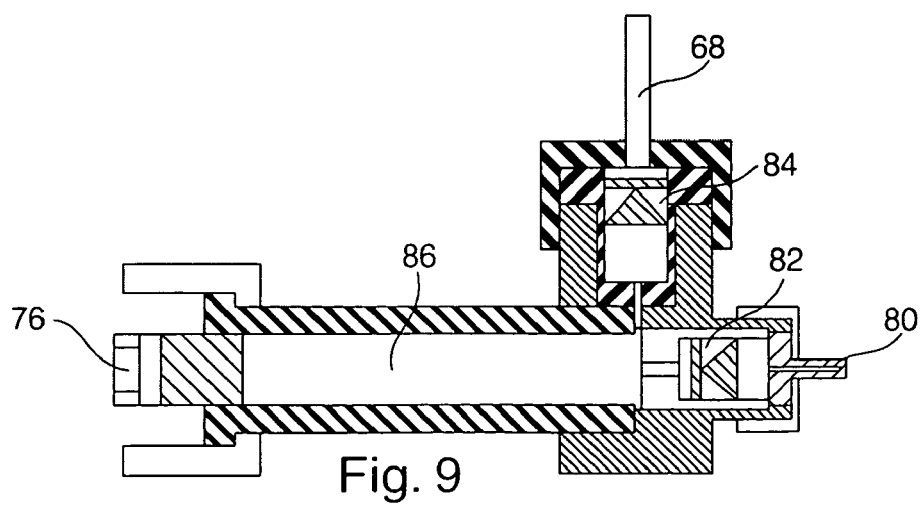
FIG. 9 is a cross section of another embodiment of the medicine chamber of the present invention.

In one embodiment, the piston rods 76 and 36 of the medicine unit 16 and the amplifier 30, respectively, move as one unit in both directions (fill and expel). For example, when pressure is applied to the piston 36 of the amplifier 30 from the air distribution unit 32, the piston 76 of the medicine unit 16 is also retracted within the high pressure chamber 86 causing the medication from the supply bottle 18 to be withdrawn into the high pressure chamber 86 and pressurized for injection. Upon activation of the injector 10, the piston rod 76 and the piston 36 are released forcing the pressurized medication within the high pressure chamber 86 through the outlet valve 84 into high-pressure hose 68 to the hand piece 20. In one embodiment, the high-pressure hose 68 has pressure capabilities of 10,000 psi or more. In yet another embodiment, the high-pressure hose 68 located between the medicine unit 16 and the hand piece 20 is 1300 mm +/−20 mm in length. FIGS. 8 and 9 depict alternate embodiments of the medicine unit 16 of the present invention, wherein the inlet valve 82 and the outlet valve 84 are located in different configurations.

Figure 10:
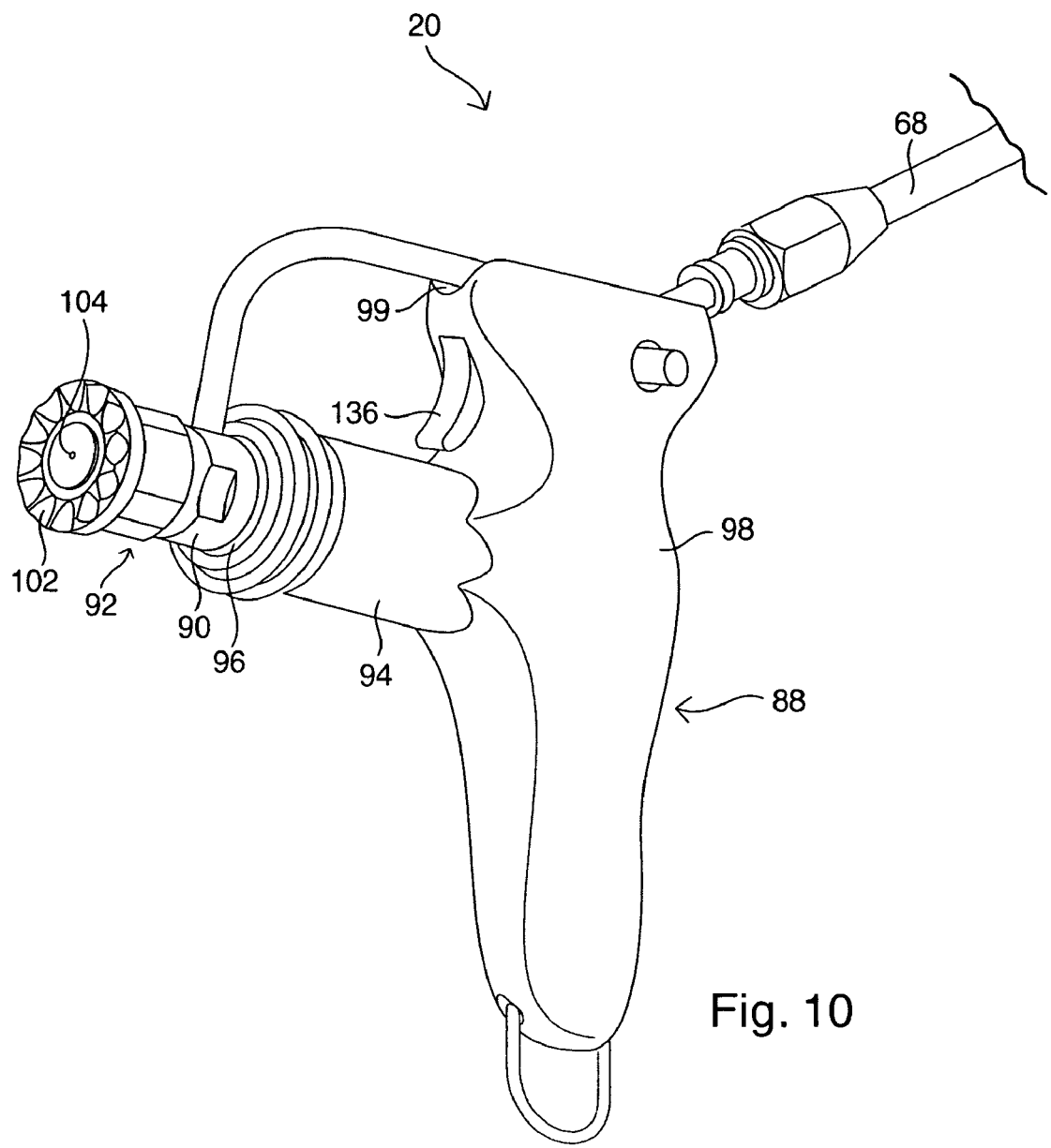
FIG. 10 is a perspective view of one embodiment of the hand piece of the present invention.
Figure 11:
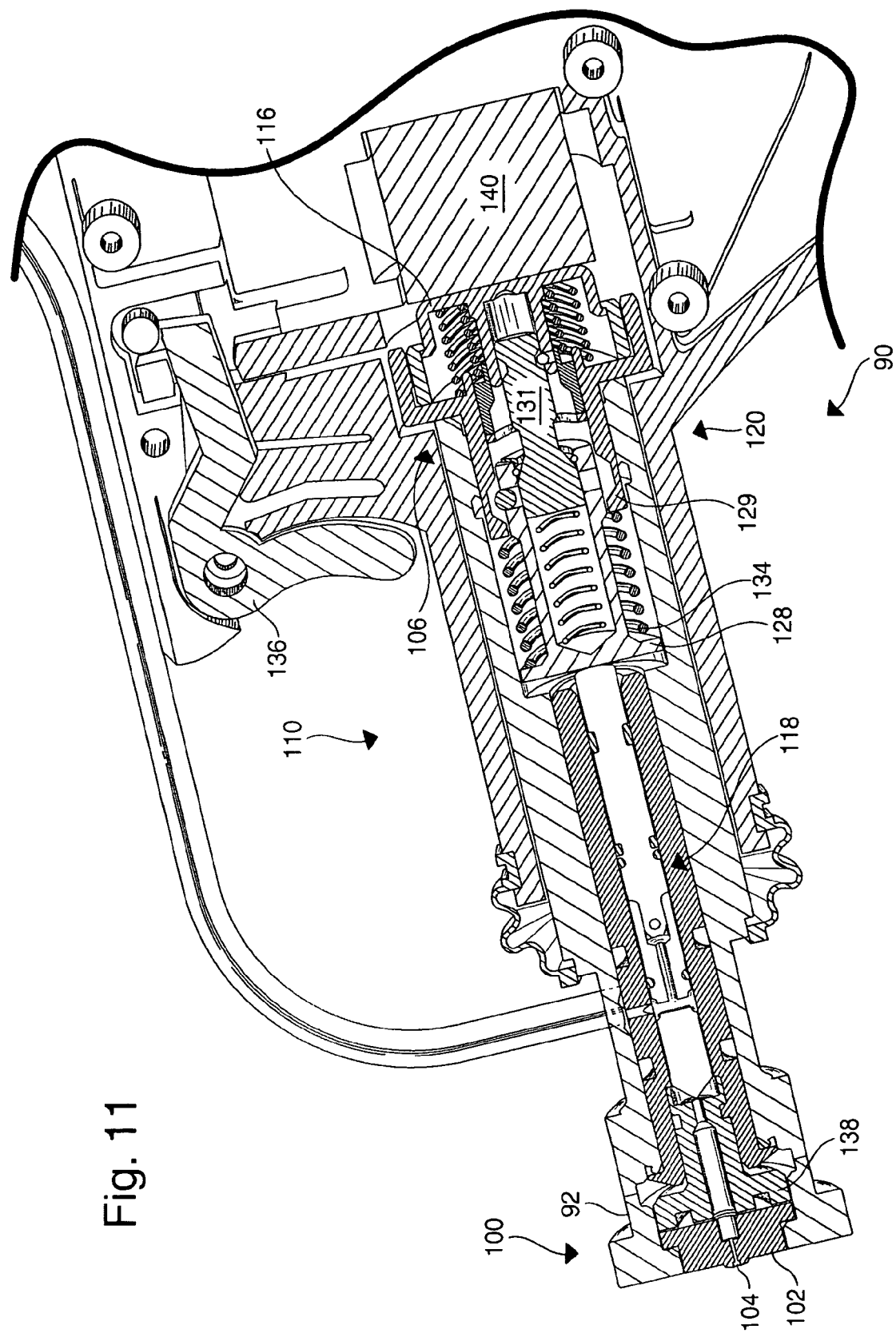
FIG. 11 is a side view of one embodiment of the core of the hand piece of the present invention.

FIG. 10 depicts one embodiment of the hand piece 20 of the present invention. The hand piece 20 includes a body 88 and a core 90. The body 88 includes a housing 94 having an open end 96 and a closed end 98. The core 90, which rests at least partially within the housing 94 of the body 88, connects to the medicine unit 16 through the high pressure hose 68. In one embodiment, the hose 68 is made of stainless steel. The body 88 of the hand piece 20 may include a channel 99 which positions the hose 68 on the body 88 of the hand piece 20 to prevent rotation of the core 90 within the body 88. The core 90 has a distal end 100 having a nozzle 102 held in place by a nozzle nut 92 and a proximal end 106 (FIG. 11). The entire core 90 may slide in the housing 94 so that the injector 10 will be actuated only when the nozzle 102 comes in contact with the subject being injected. In one embodiment, a bellows seal (not shown) may be utilized to prevent foreign material from entering the housing 94.

The nozzle 102 may be located distal to the nozzle nut 92 and has an orifice 104 that releases the medication into the subject. The velocity of medication to be injected may be controlled by varying the diameter of orifice 104 or by varying the pressure in the high pressure chamber 86. In one embodiment, the orifice 104 has a diameter of 0.2–0.36 mm. In another embodiment, the nozzle 102 includes a ruby orifice 104.

The front face of the nozzle 102 may have a textured surface. For example, in one embodiment depicted in FIG. 10, the nozzle 102 has a scalloped surface. The scalloped nozzle may be designed to ensure that there is no relative movement between the nozzle 102 and the subject. This is particularly important when attempting to vaccinate or give injections to moving subjects. In one embodiment, a protective cap (not shown) covers the nozzle 102 to prevent debris or blood from the subject from entering through the orifice 104 into the hand piece 20.

Figure 12:
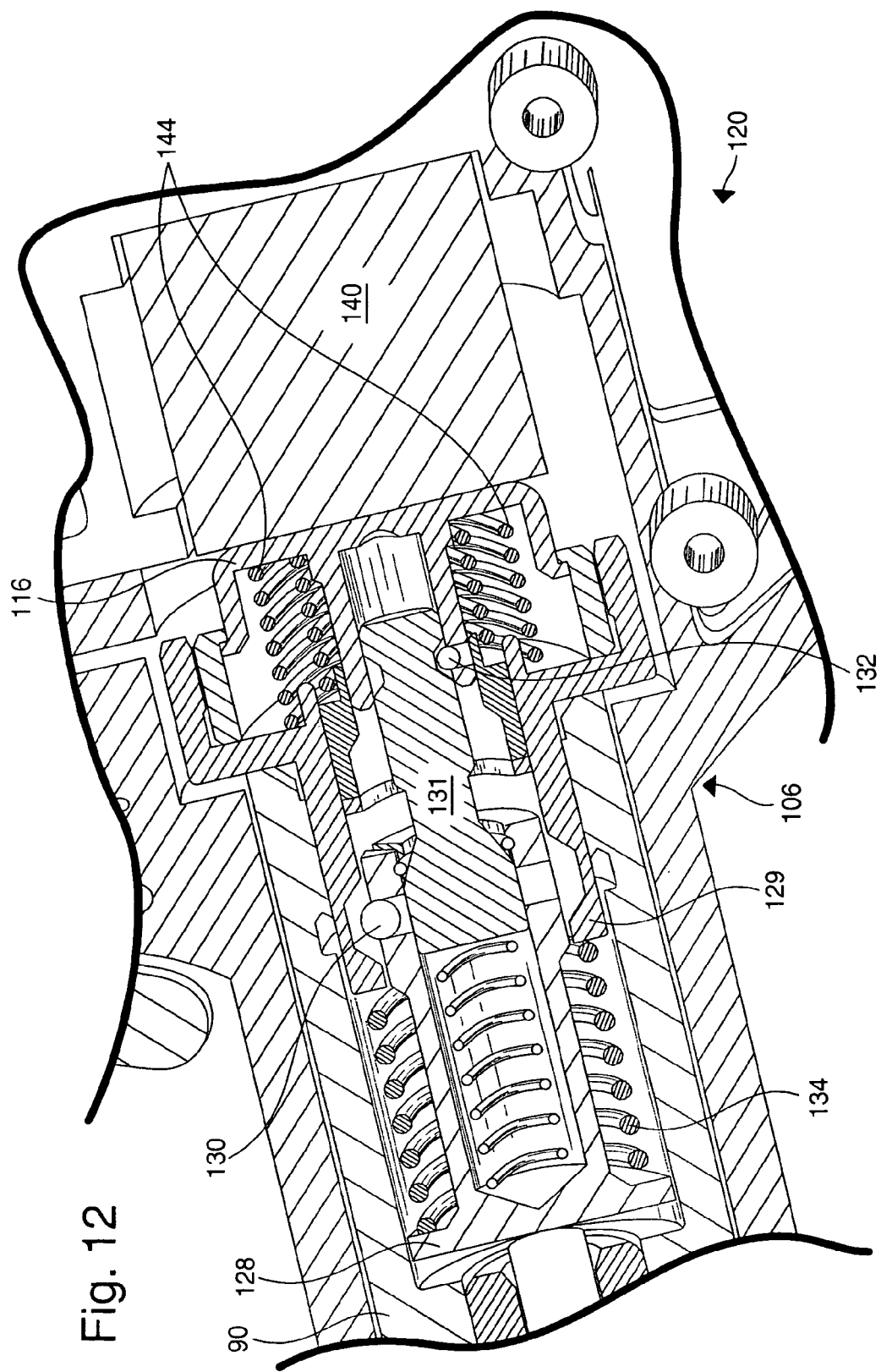
FIG. 12 is a side view of one embodiment of the ball lock assembly of the core depicted in FIG. 11.
Figure 13:
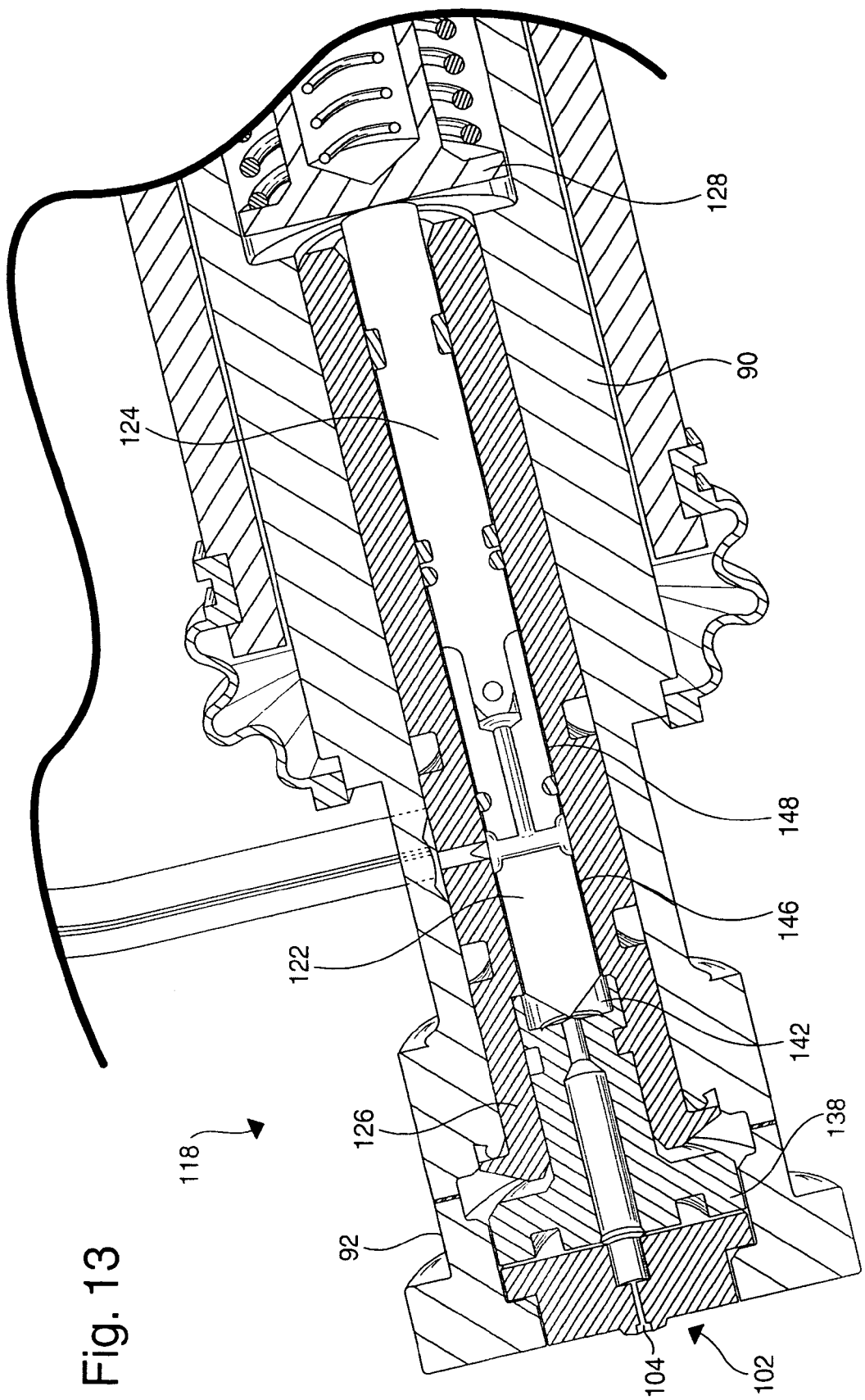
FIG. 13 is a side view of one embodiment of the needle assembly of the core of FIG. 11.

As depicted in FIGS. 11 through 13, the core 90 further includes a valve assembly 110 located within the core 90 to control the release of medicine from the medicine unit 16 to the hand piece 20 and out to the subject. The valve assembly 110 includes a front seal plug 138, a needle assembly 118 (FIG. 13), a ball lock assembly 120 (FIG. 12), and a rear housing plug 140. As depicted in FIG. 12, the ball lock assembly 120 includes a button 116 at the proximal end 106 of the core 90, a front separator 128, a first ball lock 130, a central core pin 131, a second ball lock 132, a main spring 134, and a plurality of biasing springs 144. The ball lock assembly 120 attaches to the core 90 via a ball lock frame 129. The main spring 134 is located between the front separator 128 and the ball lock frame 129.

The needle assembly 118 is located between the nozzle nut 92 and the front separator 128 (FIG. 11). Lateral movement of the needle assembly 118 within the core 90 controls the release of medicine from the hand piece 20. The needle assembly 118, depicted in further detail in FIG. 13, includes a front portion 122 and a back portion 124 housed in an insert sleeve 126 of the core 90. The back portion 124 rests against the front separator 128. The front portion rests against a saddle 142 of the front seal plug 138 when the injector 10 is not activated. The needle assembly 118 may further include pressurizing chambers 146 and 148 that must be pressurized in order to open the needle assembly 118. The front seal plug 138 provides an exit for the medication from the high-pressure hose 68 to the orifice 104 when the needle assembly 118 opens.

The needle assembly 118 is designed so that it senses pressure within the high pressure chamber 86. If the high pressure chamber 86 is not adequately pressurized (i.e. when the high pressure chamber 86 is not fully dosed), then the pressurizing chambers 146 and 148 are not pressurized and the needle assembly 118 blocks passage of the medicine from the high pressure hose 68 to the core 90 and will not open to release the medicine. When the needle assembly 118 senses an adequate level of pressure within the high pressure chamber 86, the needle assembly 118 provides a passage for the medication from the high pressure hose 68 through the hand piece 20 and out the nozzle 102.

When pressurizing chambers 146 and 148 are pressurized by the hydraulic pressure supplied from the high-pressure hose 68, movement of ball lock assembly 120 controls the opening and closing of the needle assembly 118. When the nozzle 102 is pressed against a subject, the core 90 moves toward the closed end 98 of the housing 94 causing the button 116 of the ball lock assembly 120 to contact a rear housing plug 140, thereby causing the button 116 to depress. The button 116 contacts the rear housing plug 140 by a push or pull button core concept. In the embodiment depicted in FIGS. 11–13, the core 90 pushes the button 116 into the rear housing plug 140. Depression of the button 116 against the rear housing plug 140 causes the central core pin 131 to move forward toward the distal end 100, allowing the front ball lock 130 to release into the ball lock frame 129. Release of the front ball lock 130 allows the front separator 128 to move toward the proximal end 106 of the core 90 due to the hydraulic pressure pushing on the back portion 124 of the needle assembly 1118. When the pin 131 reaches the end of the stroke toward the distal end 100, biasing springs 144 force the central pin 131 to move back toward the proximal end 16, thereby releasing second ball lock 132 and allowing the button 116, front separator 128, and central pin to move independently from each. Movement of the back portion 124 toward the proximal end 106 of the core 90 causes the front portion 122 of the needle assembly 118 to move away from the saddle 142 toward the proximal end 106. When the front portion 122 moves away from the saddle 142, the medication can flow through the seal plug 138 and exit the orifice 104.

As long as the central pin 131, front separator 128, and button 116 move independently, the injector 10 cannot be actuated again. The flow of medication continues to exit the needle valve 118 until pressure in the pressurizing chambers 146 and 148 drops below a critical level (approximately 2000 psi). When the pressure reaches this level, the main spring 134 pushes the front separator 128 into the back portion 124 of the needle assembly 118 toward the distal end until the front portion 122 reaches the seal plug 138, thereby closing the path for to the orifice 104. Once the front portion 122 of the needle assembly 118 reseats against the saddle 142, the first ball lock 130 reengages to its initial position. When the hand piece 20 is released from the patient being injected, the biasing springs 144 in the ball lock assembly 120 are released and the second ball lock 132 returns to the locked position. The first ball lock 130 cannot reopen until the button 116 is released again.

The ball lock assembly 120, as disclosed above, operates by pushing the button 116 with the sliding core 90. Alternately, the ball lock assembly 118 may be designed to operate by pulling a pin (pull core). In the pull core, the entire core 90 does not move. Instead, the core 90 may include a sliding ring at the front of the injector 10 connected to a pin extending from the core assembly with bails or push rods (not shown).

The injector 10 may be designed to operate only if the hand piece 20 is held properly. The injector 10 may be designed so that in order to give the injection to a subject, the hand piece 20 must be pushed against the subject. The correct amount of force may cause the injector 10 to fire the medication into the subject. For example, as depicted in FIGS. 11 through 13, the sliding core 90 serves as at least one level of safety to prevent injection of the medication when the hand piece 20 is not held against a subject. In another embodiment, at least one other level of safety is included wherein the injector 10 may require the operator to hold a safety 136 (FIG. 10) down to allow the injector 10 to work, so that if the user drops the hand piece 20, the injector 10 will not fire. For example, as depicted in FIG. 11, a safety 136 extends from the exterior of the housing 94 of the body 88 into the interior of the housing 94 to impede movement of the button 116 when the injector 10 is not in use. When the operator is ready to use the injector 10, the operator releases the safety 136 to permit sliding movement of the button 116. In yet another embodiment, an ON/OFF safety may be included on the hand piece 20.

The hand piece 20 may take any shape suitable for injection into a subject. The design of the hand piece 20 is not intended to be limited to the embodiments depicted in the figures. In one embodiment, the hand piece 20 has an ergonomic design to minimize repetitive hand motion and fatigue and adapted to left- or right-handed operation. An ergonomic hand piece 20 is designed to fit in the hand of the operator for ease of use. In one embodiment, the hand piece 20 may include a counter (not shown) to count each injection cycle. The counter may be resettable or non-resettable.

Figure 14:
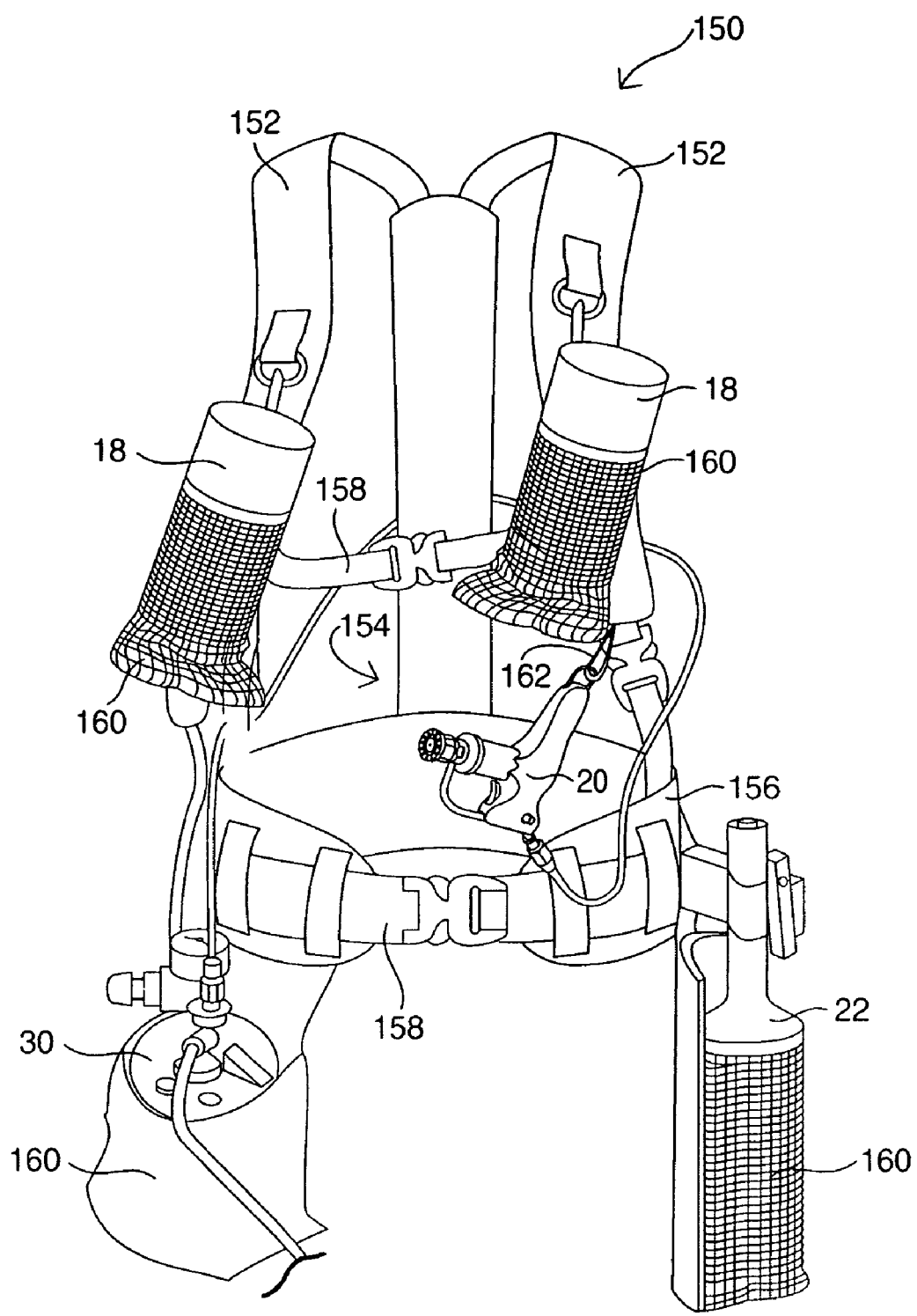
FIG. 14 depicts one embodiment of the injection system of the present invention.

In one embodiment, depicted in FIG. 14, the injector 10 is assembled and stored in an adjustable vest 150, adaptable for both right- and left-handed users. The vest 150 may be designed to assure comfortable fit and weight distribution for users of all sizes and statures. The vest 150 may include two chest straps 152 attached to a back portion 154 and a waist portion 156. Belts 158 may further secure the chest straps 152 and the waist portion 156 to the operator. The vest 150 may further include pockets 160 to accommodate the amplifier 30, the gas cylinder 22, supply bottles 18 of any size, markers, gloves, and other materials. A skilled artisan would recognize that any number of pockets 160 could be utilized with the present invention to accommodate the individual components. Further, these pockets 160 may be placed at any location on the vest 150. In one embodiment, one pocket 160 is located on each chest strap 152 to hold the supply bottles 18 and two pockets 160 are located on the waist portion 156 to hold the amplifier 30 and the gas cylinder 22. The vest 150 may also include a clip 162 that holds the hand piece 20. Any configuration of the vest 150 is foreseen including but not limited to a one-piece vest 150, resembling a clothing article that may be fastened by any type of fastener (button, zipper, ties, etc.) or a vest 150 as described above but with only one chest strap 152.

In operation, the injector 10 of the present invention is capable of performing multiple actuations. First, the operator attaches a supply bottle 18 to the medicine unit 16. Once the supply bottle 18 is connected, the power unit 14 automatically primes to the operational system pressure. The pilot valve 42 of the air distribution system 32 supplies pressure to the power piston 36 in the amplifier 30, thereby pressurizing the high pressure chamber 86 of the medicine unit 16. Once the high pressure chamber 86 is pressurized above 500 psi, the operator can approach the subject. The operator places the hand piece 20 in his hand to release the safety 136 and presses the hand piece 20 against the subject with a predetermined minimum force. In one embodiment, the predetermined minimum force is 2 psi. The predetermined minimum force, however, may be adjustable. When the pressure in the high pressure chamber 86 is at operational pressure and the nozzle 102 is pressed into the subject by the operator, core 90 applies pressure to the button 116 and causes the central pin 131 to move and disengage the first ball lock 130. The force holding the front portion 122 of the needle assembly 118 against the saddle 142 is relieved and the needle assembly 118 opens. When the needle assembly 118 opens, the medicine in the high-pressure chamber 86 is able to flow through the outlet valve 84 of the medicine unit 16, through the high pressure hose 68, through the needle assembly 118 and out the orifice 104.

As the fluid in the high pressure chamber 86 escapes, the power piston 36 is driven by the air distribution system 32 which maintains the pressure in the high pressure chamber 86 during injection. The power piston 36 continues to move forward causing a predetermined amount of medication to be dispensed until the pressure in the high pressure chamber 86 drops below minimum pressure. This occurs as the power piston 36 reaches the end of the stroke and starts to retract being pushed back by the power spring 38 in the amplifier 30. The valve assembly 110 will remain open until the pressure in the high pressure chamber 86 drops below the minimum pressure, typically 500 psi. In one embodiment, the needle assembly 118 remains open for approximately 100–200 milliseconds. Once the pressure in the high pressure chamber 86 and pressurizing chambers 146 and 148 drops below minimum, the force of main spring 134 against the needle assembly 118 overcomes the minimum pressure in chambers 86, 146, and 148 and closes regardless of whether the nozzle 102 is pressed against a subject. The hand piece 20 is then removed from the skin of the subject and the valve assembly 110 resets. As the power piston 36 returns to its initial position for the next injection, the predetermined amount of medication is drawn from the supply bottle 18 to the medicine unit 16, the high pressure chamber 86 is repressurized, and the injector 10 is ready for the next injection. If the pressure in the high pressure chamber 86 is below minimum pressure, pressing the nozzle nut 92 against the subject will not cause the valve assembly 110 to open because the force of the main spring 134 continues to overcome the minimum pressure.

The following example illustrates the methods and devices of the present inventions, which should not be construed as limiting in any way.

EXAMPLE 1

The objective of the following study was to compare the serological responses induced by vaccination, the tissue reaction and general health-related safety between traditional injection by hypodermic needle and a needle-free injection device.

Materials and Methods

Two swine weaning groups were studied and designated Trial 1 and Trial 2. Pigs were bled, tagged, tattooed and randomly assigned to treatment groups (needle-free, needle, none/control) at 4–5 weeks of age. For the hypodermic needle injections, an 18 gauge×⅝ inch (first vaccination) or 1 inch (second and third vaccinations) needle was used to ensure intramuscular deposition of the vaccines. Needles were changed at least every 6 pigs. The injector described below in Table 1 was utilized for the needle-free injections.

The pigs were vaccinated with two doses of commercial *Mycoplasma hyopneumoniae* vaccine (RespiSure®, Pfizer Animal Health) at 5–6 weeks of age and again 2 weeks later, and with a commercial pseudorabies virus vaccine (PrVac+ ®, Pfizer Animal Health) at 9–10 weeks of age. Blood samples were collected at 11–13 days after the second mycoplasma vaccination and 23–25 days after the PRV vaccination.

For safety evaluation, the pigs were weighed periodically, and injection sites were observed and palpated 2 days after each vaccination and at each bleeding. In addition, injection sites were thoroughly dissected at slaughter. Data was subjected to analysis of variance to determine statistical significance.

TABLE 1

| Characteristics | Requirement |
| --- | --- |
| Energy source | Pneumatic (Compressor) |
| Storage tank pressure range | 0.75 to 1.0 MPa (109 to 145 psi) |
| Regulated Pressure range | 0.35 to 0 70 MPa (50 to 100 psi) +/− 5% |
| Regulator repeatability | +/− 2% |
| Steady state flow rate | 7 l/min (1.9 g/min) @ 0.70 MPa |
| Jet energy | User Adjustable |
| Maximum Fluid Pressure | 70 MPa (10,000 psi) |
| Cut-off Fluid Pressure | 14 MPa (2000 psi) |
| Orifice Diameter | Changeable |
| Diameter options | 0.16–0.36 mm |
| Injection Type | Subcutaneous & Intra Muscular (Adjusted by orifice and pressure) |
| Injectable Medication supply type | Remote mounted Bottles |
| Bottle Sizes | 250, 500 & 1000 ml |
| Dosage | Changeable discrete settings (available) |
| Dose settings | 1.0, 1.5, 2 0, and 2.5 ml |
| Method of changing settings | Field interchangeable components (inserts) |
| Injection Rate | 1200 injections/hour |
| Burst rate | 4 injections/6 sec |
| Counter device to count each injection cycle | Required - six digit non-resettable |
| System Weight (w/o Injectable medication) | 7.7 kg (17 lbs) - Goal |
| Hog characteristics | |
| Age | Weaned to Breeding Stock |
| Variety | Standard market hogs |

Serological data is presented in Table 2. All pigs were seronegative for *M. hyo.* and PRV prior to vaccination. The serological responses of vaccinated pigs, regardless of injection type, were significantly greater than the control pigs (P<0.05). There was no difference between the two injection types with regard to the serological responses induced by either vaccine.

Evaluation of the injection sites at slaughter indicated no injection site lesions in pigs from any of the three treatment groups. There was no difference in weight gain between the three treatments.

TABLE 2

| Injection Trial | Type | M. hyo Test 1 | OD values Test 2 | PRV S/P Ratio |
|---|---|---|---|---|
| 1 | Needle-free injector | 0.559 | 0.407 | 1.259 |
|  | Needle | 0.515 | 0.426 | 1.124 |
|  | Control | 0.038 | 0.073 | 0.016 |
| 2 | Needle-free injector | 0.449 | 0.241 | 1.874 |
|  | Needle | 0.377 | 0.259 | 2.116 |
|  | Control | 0.075 | 0.047 | 0.037 |

The pigs injected with the needle-free injector exhibited serological responses equivalent to those achieved with a needle injection. Further, injection with the needle-free injector did not result in more tissue damage when compared to conventional needle injection. Similar responses have been observed in trials with combination vaccines containing inactivated $M.$ $hyo.$ and other viral and bacterial antigens.

Although the present invention is described by reference to a single and exemplary embodiment, and the best mode contemplated for carrying out the present invention has been shown and described, it is to be understood that modifications or variations in the structure and arrangements of this embodiment other than those specifically set forth may be achieved by those skilled in the art and that such modifications are to be considered as being within the overall scope of the present invention. It is to be further understood that the following pending patent applications owned by the assignee of the instant application are hereby incorporated by reference in their entirety as if fully set forth herein: U.S. Ser. No. 09/685,499; PCT/US00/41122; U.S. Ser. No. 09/685,633; PCT/US00/27991; U.S. Ser. No. 09/717,548; PCT/US00/32186; U.S. Ser. No. 09/717,559; PCT/US00/32187; U.S. Provisional Patent Application No. 60/329,082 filed on 12 Oct. 2001; and U.S. patent application Ser. No. 10/269,5848, entitled "Universal Protector Cap with Auto-Disable Feature for Needle-Free Injectors," filed Oct. 11, 2002.

We claim:

1. A jet injector for administering a medicine to a subject, comprising:
a hand piece having a body and a core;
a medicine unit in fluid communication with the hand piece to supply the medicine at a high pressure to the core of the hand piece, the medicine unit having a high pressure chamber;
a power unit connected to said medicine unit for creating high pressure in the high pressure chamber, the power unit having an amplifier and an air distribution system; and
an energy unit having a gas cylinder, wherein the energy unit supplies gas to the air distribution system of the power unit;
wherein the high pressure medicine supplied to the core of the hand piece is at a pressure sufficient to create a jet for injecting the medicine into the subject.

2. The injector of claim 1, further comprising a supply bottle in communication with the medicine unit, wherein the supply bottle supplies the medication to the medicine unit.

3. The injector of claim 1, wherein the hand piece further comprises a valve assembly located in the core for controlling the release of medication from the medicine unit to the hand piece.

4. The injector of claim 3, wherein the valve assembly comprises a ball lock assembly and a needle assembly, wherein release of the ball lock assembly provides for movement of the needle assembly to release the medicine out of the core of the handpiece.

5. The injector of claim 4, wherein the ball lock assembly comprises a button.

6. The injector of claim 5, wherein activation of the button causes the ball lock assembly to release.

7. The injector of claim 6, wherein the ball lock assembly further comprises a first ball lock, a main spring, and a second ball lock, wherein the first ball lock controls the release of the main spring and the second ball lock controls reactivation of the injector.

8. The injector of claim 4, wherein movement of the needle assembly controls the release of the medication from the medicine unit to the hand piece.

9. The injector of claim 5, wherein the hand piece further comprises a safety in communication with the button, wherein when the safety is engaged, the button cannot release the ball lock assembly.

10. The injector of claim 5, wherein when the core is pressed against the subject, the core contacts the button.

11. The injector of claim 10, wherein the core is configured to push the button to open the valve assembly.

12. The injector of claim 10, wherein the core is configured to pull the button to open the valve assembly.

* * * * *